US005658303A

United States Patent [19]
Koepnick

[11] Patent Number: 5,658,303
[45] Date of Patent: Aug. 19, 1997

[54] UNIVERSAL AUTOMATED KERATECTOMY APPARATUS AND METHOD

[76] Inventor: Russell G. Koepnick, 4435 N. 78th St. #113A, Scottsdale, Ariz. 85251

[21] Appl. No.: 508,114

[22] Filed: Jul. 27, 1995

Related U.S. Application Data

[63] Continuation-in-part of Ser. No. 441,789, May 16, 1995, which is a continuation-in-part of Ser. No. 245,228, May 17, 1994, Pat. No. 5,496,339.

[51] Int. Cl.$^6$ .................................................. A61B 17/00
[52] U.S. Cl. ............................................ 606/166; 128/899
[58] Field of Search .................................. 606/108, 166, 606/167; 128/899

[56] References Cited

U.S. PATENT DOCUMENTS

| | | |
|---|---|---|
| 4,662,370 | 5/1987 | Hoffman et al. . |
| 4,884,570 | 12/1989 | Krumeich et al. . |
| 5,133,726 | 7/1992 | Ruiz et al. . |
| 5,288,292 | 2/1994 | Giraud et al. . |

Primary Examiner—Michael Powell Buiz
Assistant Examiner—William Lewis

[57] ABSTRACT

A surgical device for altering the curvature of an eye includes a base which carries a transparent insert, a drive device, a knife edge coupled to the drive device and movable to a plane immediately adjacent the under surface of the transparent insert. The transparent insert includes a face having a surface portion shaped according to a predetermined correction. The base further includes a suction ring which forms a vacuum chamber with the eye. The suction ring is placed against the eye. Application of vacuum results in the cornea of the eye being urged into engagement with the shaped surface portion. Actuation of the drive device moves the knife edge whereby the cornea is cut. Only the knife edge traverses the insert. In a surgical procedure, a lamellar flap is first cut to remove the epithelium, and a second prescriptive cut is made to excise a disk to provide the prescriptive correction.

13 Claims, 9 Drawing Sheets

UNIVERSAL AUTOMATED KERATECTOMY APPARATUS AND METHOD

RELATED APPLICATIONS

This application is a continuation-in-part of U.S. patent application Ser. No. 08/441,789 filed May 16, 1995 for Universal Keratectomy Apparatus and Method, pending which is a continuation-in-part of U.S. patent application Ser. No. 08/245,228 filed May 17, 1994 for Universal Keratectomy Apparatus and Method, now U.S. Pat. No. 5,496,339.

Other related applications are U.S. design patent application filed Jul. 26, 1995 for Refractive Surgery Device; U.S. design patent application filed Jul. 26, 1995 for Myopic Corrective Insert for Refractive Surgery Device; U.S. design patent application filed Jul. 26, 1995 for Lamellar Corrective Insert for Refractive Surgery Device; U.S. design patent application filed Jul. 26, 1995 for Hyperopic Corrective Insert for Refractive Surgery Device; and U.S. design patent application filed Jul. 26, 1995 for Knife Edge for Opthalmic Refractive Surgery Device.

BACKGROUND OF THE INVENTION

This invention pertains to an opthalmic surgical device and to methods for performing corrective refractive surgery on eyes. One of the first procedures for refractive surgery was the Barraquer microkeratome which placed against the cornea a flat applanate surface supported with the knife (as in a plane) guided by spaced apart dovetailed guides which formed rails on a suction ring applied to the sclera and then manually passed across the cornea at an angle thereto a power driven reciprocating knife edge in a guideway to remove a round lamellar (sides parallel to the surface of the cornea) disk. The thickness of the cut disk was controlled by the thickness of a spacer plate (numerous plates for various thicknesses) and the cut disk rolled up into a groove between the spacer plate and the block carrying the knife as the cut was made. The cut disk was then frozen, lathed and replaced. The procedure was known as keratomileusis.

Mechanical devices known as keratomes have been utilized to perform multiple lamellar cuts of the cornea. In this procedure, a first disk is cut. Then a second smaller disk is cut and removed. The first disk is sewn back on. This procedure, known as keratomileusis in-situ, eliminated the freezing process and overcame many of the problems of the keratomileusis procedure. However, keratomes still lacked precision, predictability and the ability to make smooth corneal cuts.

Microkeratomes, for example, Giraud et al U.S. Pat. No. 5,288,292, applicant being a co-inventor thereof, have replaced Barraquer's multiple spacer plates for controlling the thickness of the cut with a single adjustable plate which controls the space between the plate and knife edge and, hence, the slice thickness. Micrometers have been placed on the microkeratome to precisely control the thickness.

The procedure known as radial keratotomy is used extensively for the correction of low to medium myopia and astigmatism. The procedure involves changing the shape of the cornea by making deep corneal cuts which are 80–90% of corneal thickness extending out from a central optical zone of about 3 mm diameter. While many patients report satisfactory results, others are bothered by regression and many experience a starburst effect from the reflection of light at nighttime when the pupil is dilated larger than 3 mm. The scars from the deep corneal incisions scatter light at night time. Radial keratotomy is usually limited to about 8 diopters of refractive correction.

Eximer lasers have been used for corneal sculpturing for correction of myopia and astigmatism. The eximer laser ablates (removes by vaporization) the cornea in a manner that results in removing a lenticular (sides not parallel to the surface of the cornea) disk from the cornea with a diameter of about 5–6 mm. The procedure requires that the epithelium (thin outer layer of the eye) be scraped off. Then the eximer laser ablates the cornea in a series of stepped ablations which leave a less than smooth surface on the corneal bed. The procedure subjects patients to substantial pain for a few days and obstructed vision for months. The use of eximer lasers to remove superficial irregularities of the cornea has met with mixed success due to ablation induced hyperopic shifts of corneal refraction.

U.S. Pat. No. 4,662,370 shows a device in which the adjustable movable plate of the earlier devices has been replaced by a fixed plate. This device begins the cut of the cornea outside of the correction zone, passing superstructure over the cornea blocking the surgeons view during the cut, and requires the complexity and cost of multiple vacuums chambers.

There remains a long felt need for a smooth cutting keratome that can be used for all defective vision corrections including those requiring irregular cuts, cuts only under a prescribed, predetermined corrected surface and which provides automated advance without blocking the surgeon's vision during the cut.

SUMMARY OF THE INVENTION

A surgical device in accordance with the principles of the invention alters the curvature of an eye by cutting a corneal disk with a knife edge which is advanced under a transparent member or insert which has a surface portion adjacent the plane of movement of said knife edge shaped according to a predetermined prescriptive correction. The device is configured such that only the knife traverses the eye so that the surgeon can observe cutting by the knife through the transparent insert during the entire procedure. Further in accordance with the principles of the invention, the knife edge is reciprocated from side to side at high speed to facilitate the smooth cutting of the tissue.

The device includes a suction ring which is positioned and held against the sclera of the eye with the corrected surface portion of the transparent member touching the cornea of the eye.

Further in accordance with the invention the suction ring device and a sclera of an eye when received therein form the single and sole annular vacuum chamber in the entire assembly.

The transparent member is easily replaceable as an insert and has a visible crosshair image for aligning the insert with the cornea prior to cutting.

The invention has many advantages over other mechanical keratomes, eximer lasers and radial keratectomy. One major advantage is that surgery utilizing the device is reversible. Reversibility can be accomplished by simply replacing the excised corneal disk or by excising another disk from a donor cornea using the same insert as used for the original operation. An additional advantage is that highly accurate prescriptive corrective cuts can be made.

In accordance with the principles of the invention, a method of corrective eye surgery is provided in which a mechanical resection of meniscus shaped lenses allows for an accurate, optically correct technique for the correction of refractive errors.

In accordance with the principles of the invention, an optically correct, mechanical technique for attaining emmetropia is provided. In the method of the invention, a desired prescriptive correction is determined. From the desired correction, an equivalent powered plano lens shape is calculated. The negative image of the equivalent lens shape is formed into a keratome insert. The insert is centered on the eye. A vacuum is applied to the eye to urge the cornea of the eye into contact with the insert forcing the cornea into the cavity created in the insert. A reciprocating knife edge traverses the insert removing the tissue in the insert cavity. After releasing the vacuum, the cornea returns to a natural shape and the removal of a lenticular tissue has been achieved.

Further in accordance with the principles of the invention, a surgical procedure with significant improved results over prior procedures is practiced with the keratome device of the invention. In the procedure, a disk shaped flap is first cut to remove the epithelium. Subsequently, a corrective cut disk is removed from the cornea. The epithelium flap is then replaced.

In one procedure, the flap cut is cut as a lenticular cut disk thereby providing tapered edges to facilitate healing. In yet another procedure, the flap cut is a lamellar cut. In either instance, the second disk cut from the eye is shaped to provide the desired level of correction to the eye.

BRIEF DESCRIPTION OF THE DRAWINGS

The invention will be better understood from a reading of the following detailed descriptions of embodiments of the invention taken in conjunction with the drawings in which.

DETAILED DESCRIPTION

The change in the corneal surface using the surgical device of the present invention will be determined by an optical correction formed into a custom made member or insert based upon a doctor's prescription. The prescription is similar to the prescription a doctor might give to an optical laboratory for the purpose of grinding lenses for eye glasses or for contact lenses.

Figure 1:
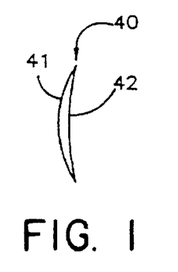
FIG. 1 is a schematic section of a lenticular corneal disk cut.
Figure 2:
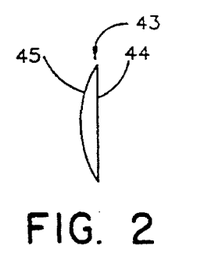
FIG. 2 is the optical equivalent of FIG. 1 in plano-convex form.
Figure 3:
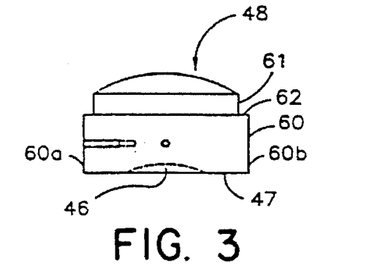
FIG. 3 is a transparent insert of the present invention with a concave prescriptive correction formed into its bottom surface.

FIG. 1 illustrates a particular prescribed corrective portion which is to be removed from a patient's eye. This lenticular cut portion 40 which is to be removed from an eye has two surfaces 41, 42 which form a positive meniscus (crescent) in shape. This prescriptive correction is mathematically converted to the optical equivalent 43 seen in FIG. 2. Equivalent 43 has a planar side 44 and a convex side 45. In accordance with the invention, the optical prescription is sculpted into a flat face 47 of an insert 48 shown in FIG. 3. The insert 48 is then inserted into applicant's instrument which is placed against the eye and an equivalent cornea portion of the eye is cut off thereby altering the curvature of the cornea by precisely the prescribed amount. The prescriptive member or insert 48 as shown in FIG. 3, has surface 47 profiled to correspond to the plano convex shape of FIG. 2. As shown in FIG. 3, corrective portion 46 of the insert 48 corresponds to the equivalent shape 43.

The insert 48 is carried by a device 110 shown in its entirety in FIG. 25 and which is described in greater detail below. The device 110 serves to hold the insert 48 in position on an eye while a knife blade is passed under the insert and immediately adjacent thereto. In accordance with the invention a vacuum chamber is formed by the device 110 and the eye adjacent to the lower surface of the insert 48. Application of partial vacuum to this chamber raises the innerocular pressure of the eye causing the cornea of the eye to be urged into contact with the prescriptive portion of the insert 48.

Figure 4:
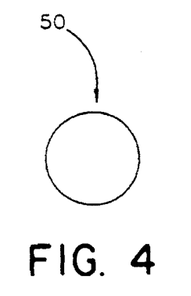
FIG. 4 is a schematic of the cornea of an eye before vacuum is applied.
Figure 5:
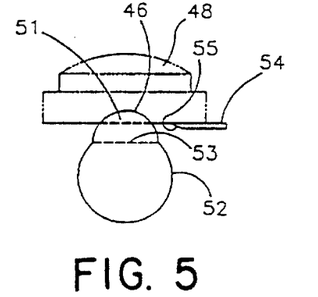
FIG. 5 is a schematic of the cornea with the vacuum applied.
Figure 6:
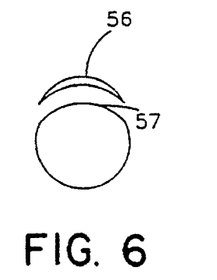
FIG. 6 is a schematic of the cornea after the cut with the vacuum off.

FIGS. 4, 5, and 6 illustrate the sequence of operation on an eye in schematic form. The eye 50 is shown schematically without the device of the present invention in FIG. 4. In FIG. 5 the surgical device 110 which is not shown is placed into contact with the eye and a partial vacuum is applied to the sclera 52. The vacuum is adjusted to a level such that forces are applied to the cornea 51 by the suction ring raising the innerocular pressure in the eye 50 and forcing the eye to bulge outwardly causing the cornea 51 to fill the prescriptive concave depression 46 of the insert 48. The portion of cornea 51 filling the depression 46 in the insert 48 is rapidly but smoothly excised by a knife 54 oscillating from side to side. Knife 54 is advanced across the eye at a predetermined rate in a plane parallel and adjacent to the flat face 47 of the insert 48. The knife 54 has a knife edge which is flat on its upper surface and concave on its lower surface 55.

After the cut has been made, the partial vacuum is released. As shown schematically in FIG. 6, when the vacuum is released the cornea 51 will return to its normal shape less the disk portion 56 excised by the cut. The disk 56 is of a lenticular cut of the required refraction so that the remaining cornea 57 has precisely the proper refractive power for emmetropia (normal vision).

With the present invention, highly precise corrections may be made because highly precise sculpting or grinding apparatus are commercially available to form the prescriptive corrective recess in the inserts. These apparatus in combination with computer technology allow forming the recess of the insert 48 to within two tenths of a micron.

The insert 48 may be alternatively provided with a convex, planar or irregular correction formed into the flat face 47 of the insert 48 to provide corresponding corrective cuts in the cornea.

The insert of FIG. 3 is of generally cylindrical shape having outer walls 60, 61 of different diameters to provide a shoulder 62. To permit precise registration of the insert in the surgical device, registrators 63, which are tapped holes in the insert 48 receiving pins or screws, index the corrected surface 46 to the surgical device so that the prescriptive surface 46 may be aligned with a predetermined optical portion of the eye. The registrators 63 may be more clearly seen in FIGS. 7 and 8. Other equivalent registrators may be utilized such as slots and lugs.

Figure 7:
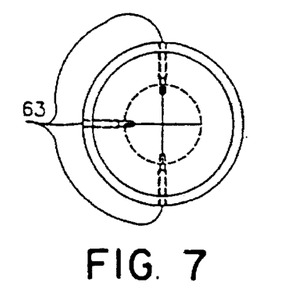
FIG. 7 is a top view of the insert of FIG. 3.
Figure 8:
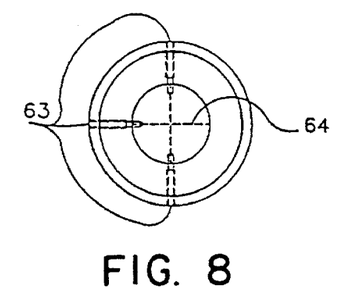
FIG. 8 is a bottom view of the insert of FIG. 3.

Visual positional alignment is achieved using crosshairs 64 as shown in FIGS. 7 and 8 which allows the surgeon to look through the insert to align the crosshairs 64 with the optical center of the eye after which the vacuum is applied. Insert 48 is transparent and is preferably made of an acrylic plastic such as the well known PMMA. Equivalent materials include materials used for the manufacture of eye glasses or hard contact lens.

Figure 9:
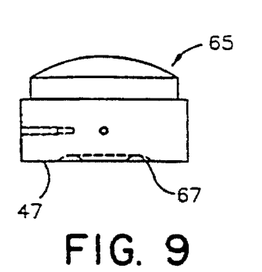
FIG. 9 is an elevation view of an optical insert with a prescriptive concave correction.
Figure 10:
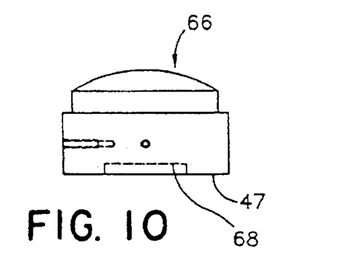
FIG. 10 is an elevation view of an optical insert with a planar correction.

Other corrections may be made utilizing the surgical device of the invention. FIGS. 9 and 10 illustrate inserts having different prescriptive corrections. Insert 65 shown in FIG. 9 has a convex correction 67 formed into flat face 47. Correction 67 will produce a disk which is of reduced thickness centrally to correct hyperopia.

Irregular corrections for such defects as astigmatism may be formed into the insert 48 by means of a laser or by use of optical grinding machines. Thus, the refractive correction for any degree of myopia, hyperopia, or astigmatism can therefore be precisely and predictably formed into an insert.

Insert 66 shown in FIG. 10 has a recess 68 which will produce an essentially lamellar cut disk of any desired thickness or diameter. It will be understood by those skilled in the art that although the descriptions provided herein identify the insert 48 which has a particular prescriptive correction, the inventive device will work with inserts having other prescription corrections.

The surgical device 110 shown in FIG. 25 will now be described in detail with reference to other drawing figures.

Figure 11:
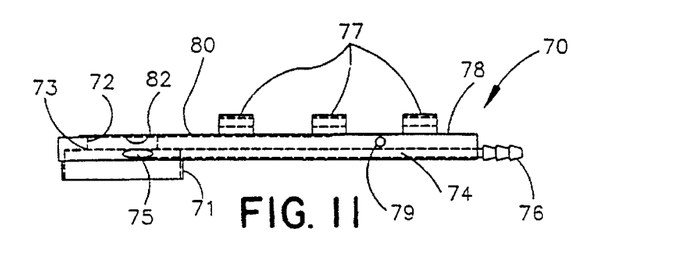
FIG. 11 is a front elevation view of the suction ring and blade guide.
Figure 12:
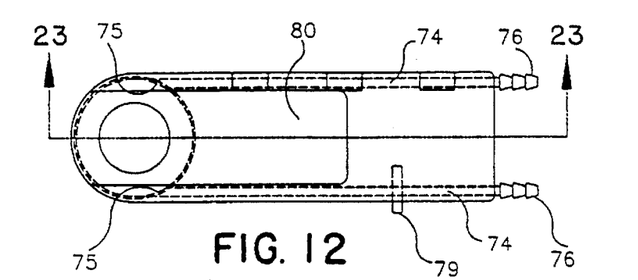
FIG. 12 is a top view of FIG. 11.
Figure 13:
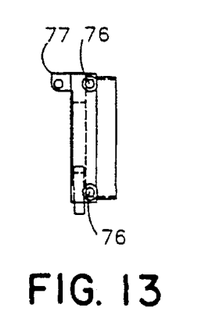
FIG. 13 is a right side view of FIG. 12.

In FIGS. 11, 12 and 13 a suction ring and blade guide member 70 includes a suction ring 71. The suction ring 71 has a stepped portion such that the inner portion 72 has an inner diameter smaller than inner diameter of the portion 71. A square corner or shoulder 73 is thereby formed whereby a force will be exerted against the sclera of the eye when the device is placed on the eye and a partial vacuum is applied. In addition, the peripheral edge of the suction ring will contact the eye also exerting force against the eye. The eye will react to the forces by producing equilibrium forces which will cause the eye to bulge outwardly. A cornea portion 51 will be thereby urged completely against the prescriptive shaped surface portion 46 of the insert 48 for the cutting operation. The inside diameter of the portion 72 of the suction ring 71 adjacent the insert 48 is smaller than the outside diameter 60 of insert 48 adjacent the suction ring portion 72. Thus, in the present invention, the knife 54 will cut the cornea in a plane immediately under and adjacent the shaped surface portion 46 of the insert 48. Vacuum passages 74 in the outboard ends of member 70 exit at ports 75 in ring 71 at one end and in barbed tubes 76 at the other end. Bored hinge posts 77 extend above the upper surface 78 of member 70 and are rotatably received within recesses 96 in the first insert holder 90 to form an internal hinge coupling the suction ring 71 to the first holder 90. Post 79 receives clasp 97 to latch the ring 71 to the holder 90.

Figure 14:
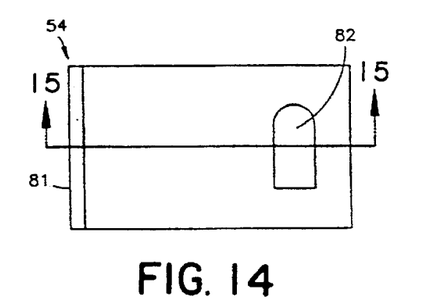
FIG. 14 is a top view of a knife.
Figure 15:
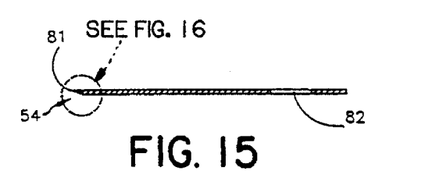
FIG. 15 is a section view of the knife of FIG. 14 taken along line 15—15.
Figure 16:
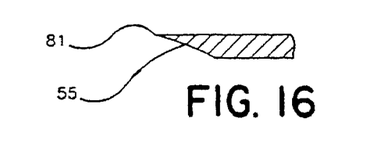
FIG. 16 is an enlargement of the circled portion of the knife FIG. 15.

As seen in FIGS. 11 and 12 recess 80 in the upper surface of member 70 forms a flat blade guide for the flat knife 54. A knife guide recess 80 is in a plane in the suction ring and blade guide member 70 parallel to and immediately adjacent to the face 47 of the insert 48, as more fully described below. The knife 54 shown in FIGS. 14, 15 and 16 is advanced slideably from right to left in FIG. 12 and is reciprocated from side to side as it is advanced in the recess 54.

Knife 54 has edge 81 which is movable transverse the eye 50 to cut only the corneal tissue 51 under an insert 48. In particular, only the corneal tissue 51 under the prescriptive surface portions of the insert 48 is cut. The knife edge is concave in its bottom surface portion 55. The knife 54 has a lug opening 82 therein, as more fully described below.

In this embodiment, knife 54 is preferably made of stainless steel. The knife 54 is of such length that it will extend in the recess 80 of FIG. 12 sufficiently in advance of the superstructure of the drive mechanism which drives and advances the knife whereby the only portion of the device which passes over the eye during the cutting operation is the knife 54.

Figure 17:
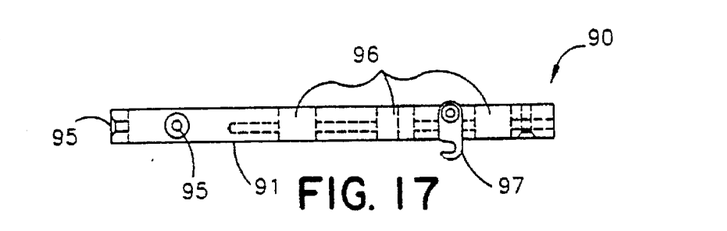
FIG. 17 is a front elevation of a first portion of an insert holder and motor brace.
Figure 18:
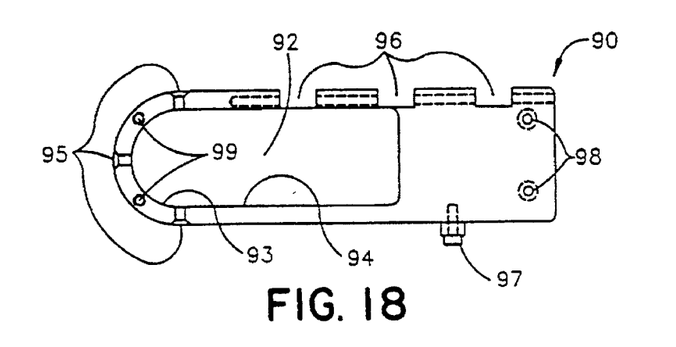
FIG. 18 is a top view of FIG. 17.
Figure 19:
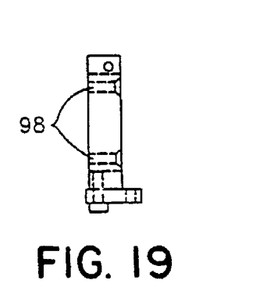
FIG. 19 is an end elevation view of FIG. 18.

Turning now to FIGS. 17, 18 and 19 a first insert holder 90 has a planar surface 91 adjacent the suction ring recess 80. The planar surface 91 is non-adjustable relative to the recess 80 and has an opening 92 for receiving and holding the insert 48. The face 47 of insert 48, except for the prescriptive surface portion 46 lies coplanar to the planar surface 91. The cutting edge 81 of knife 54 is as shown in FIG. 25 contiguous the planar surface 91. The knife 54 is guided by a bottom surface 82 of the recess 80 shown in FIG. 11 and the planar surface 91.

Opening 92 in insert holder 90 has left inner wall portion 93 shown in FIG. 18 which will touch a first portion 60a, shown in FIG. 3, of the outer surface 60 of the insert 48 adjacent the knife 54. Opening 92 has inner wall portions 94 shown in FIG. 18 which are open to the atmosphere relative to a second portion 60b of the outer surface 60 of the insert 48 as shown in FIG. 3 adjacent the knife 54 as shown most clearly in FIG. 25. The first and second portions 60a, 60b are each substantially half of the outer surface of the insert adjacent the knife.

Figure 20:
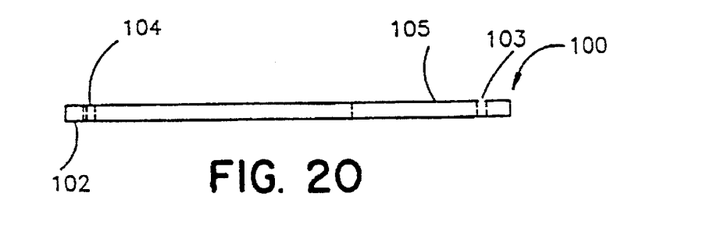
FIG. 20 is a front elevation view of a second portion of an insert holder and motor brace.
Figure 21:
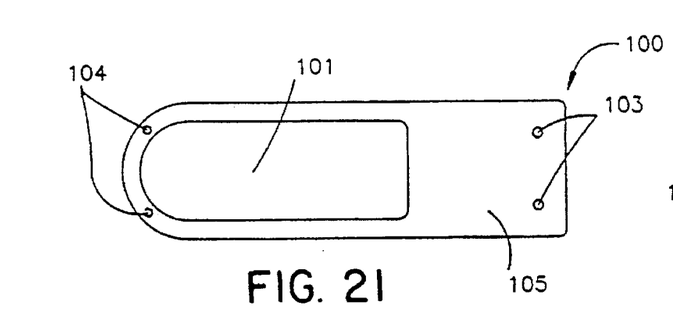
FIG. 21 is a top view of FIG. 20.
Figure 22:
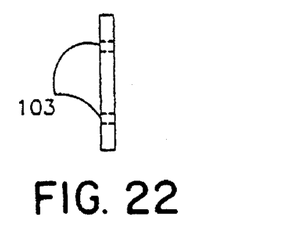
FIG. 22 is a side elevation of FIG. 21.
Figure 24:
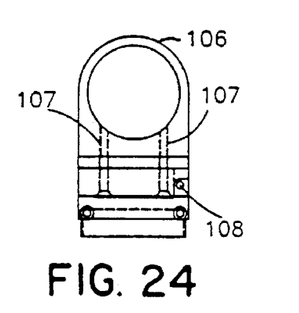
FIG. 24 is a side elevation of FIG. 23.

The holders 90 and 100, insert 48 and suction ring and blade guide 70 form a single assembly 140 as shown in FIG. 24. Holder 90 is shown in detail in FIGS. 17, 18, and 19, and holder 100 is shown in FIGS. 20, 21, and 22.

Figure 23:
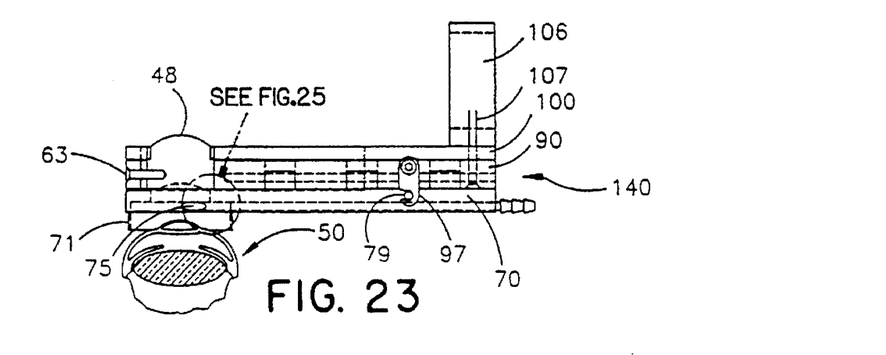
FIG. 23 is front elevation of the holder suction ring assembly invention with insert and a schematic of the eye to which the assembly is to be applied.
Figure 25:
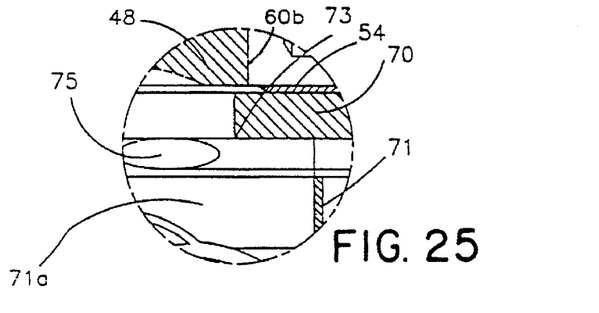
FIG. 25 is a sectional blow-up of the circled portion of FIG. 23 in partial section along the line 25—25 of FIG. 12.

As shown in FIGS. 23 and 25 vacuum ports 75 exit at the upper portion of the inner surface of ring 71, an area not contacted by the inserted sclera 52. Thus, the suction ring 71 and the sclera 52 of an eye 50 when received therein form a single and sole annular vacuum chamber 71a, shown most clearly in FIG. 25, in the assembly between the holder 90 and insert 48, on the one hand, and the eye 50, on the other hand. The vacuum chamber is coupled via port 75, recess 74, barbed tubes 76, and a vacuum line 131 to a vacuum source 133 as shown in FIG. 25 for holding the assembly 140, 110 against the sclera 50 shown in FIGS. 23 and 25 during the operation.

The vacuum at port 75 is adjustable by knob 132 at control console 130 allowing the surgeon to view the cornea 51 under the insert 48 and preferably adjust the vacuum to the precise point where the cornea 51 only contacts the corrected portion 46 of insert 48 at the time of the cut.

As most clearly shown in FIGS. 23 and 25, first holder 90 includes registration holes 95 which receive pins or screws to secure insert 48 in recess 92 of holder 90. The corrected surface 46 is indexed to the position 59 it had relative to the eye when the prescriptive correction was measured and subsequently formed into the insert 48.

Recesses 96 are part of the hinge mechanism and with a hinge pin 108 shown in FIG. 24 rotatably receive hinge posts 77 shown in FIGS. 11 and 13 to form an internal hinge. Clasp 97 releases suction ring and blade guide member 70 allowing it to swing open downwardly. Thus, the member 70 is coupled to the insert holder 90 for inserting and removing the cutting blade 54 and the insert 48 from the first holder 90, or for removing the cut disk 56 from between the upper surface of the knife 54 and the prescriptive surface 46 of an insert 48 after an operation is performed, and the knife 54 is retracted.

As best seen in FIG. 23, however, the first insert holder 90 is positioned adjacent the suction ring and blade guide 70. The second insert holder 100 is positioned adjacent the first insert holder 90. The insert 48 is received and held between the first and second holders 90 and 100 to form a unitary assembly 140. Opening 101 in holder 100 is of smaller width than recess 92 in holder 90. The shoulder 62 of insert 48 abuts against the bottom surface 102 of holder 100 retaining the insert 48 in the first holder 90. Holders 90 and 100 are held together by screws (not shown) in holes 99, 104 in holders 90, 100 and screws 107 in holes 98, 103 in holder 90, 100, respectively.

As shown in FIGS. 23 and 24, a motor bracket 106 is attached to the upper surface 105 of the second holder 100 via screws 107 in holes 98, 103.

As shown in FIG. 25, the bracket 106 is attached to a surface 105 of the holder 100 away from the suction ring 71. Bracket 106 fixedly holds a housing 112 within which an electromechanical advancer 111 and motor 113 are slidably mounted for moving the knife 54 between retracted and advanced positions at a predetermined rate.

The entire holder assembly 140, including suction ring and blade guide 70, holders 90, 100 and bracket 107 are made of titanium alloy.

Figure 26:
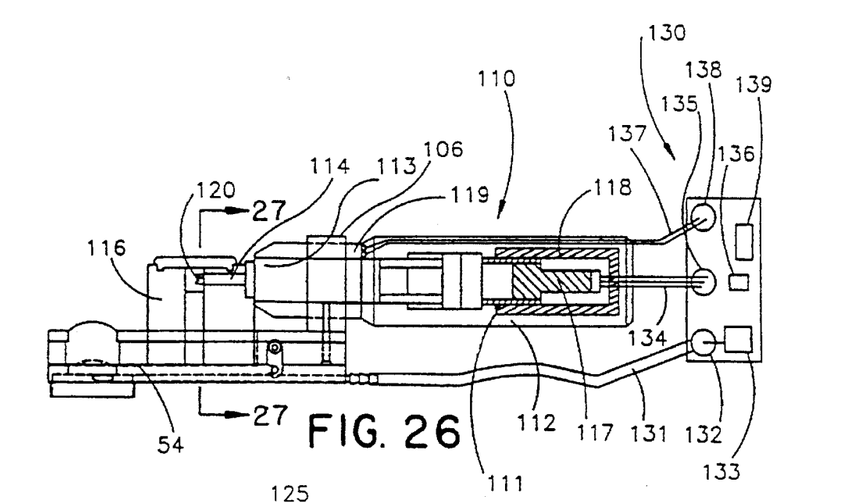
FIG. 26 is a front elevation in partial section of the complete assembly of a first embodiment of the present invention including the drive and advance mechanisms and control console.
Figure 27:
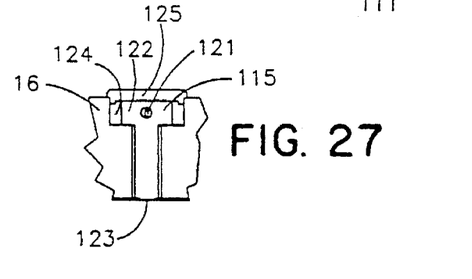
FIG. 27 is a sectional view along the line 27—27 of FIG. 26.

In the complete assembly 110 as shown in FIGS. 26 and 27, an electromechanical advancer 111 is slidably mounted within a housing 112. Advancer 111 is coupled to knife 54 through motor 113 which is slidably mounted within housing 112, shaft 114, T-cam 115 and cam block 116. The housing 112 may be either a unitary housing or a dual piece held together by clamps which are not shown. The electromechanical advancer 111 is, in this embodiment, a voice coil actuator. Due to the field of permanent magnet 118, the axial force generated upon coil 117 when current flows through the coil 117 produces relative motion between the field assembly and the coil 117. The lateral linear force pushes the motor 113 within its housing 119, the shaft 114, the block 116 and the knife 54, advancing the knife to make the cut. The rate of advance is a function of the current in the coil of the actuator 111. Motor 113 may be a standard variable speed motor.

Also shown in FIGS. 26 and 27 are drive motor 113, a rotatable shaft 114, an eccentric 120, a cam slot 121, a T-shaped cam 122, a cam lug 123, T-shaped slot 124 and the screw cap 125. The rotatable shaft 114 is driven by the motor 113 in housing 112 which is fixedly mounted to the bracket 106. Shaft 114 terminates in an eccentric portion 120.

Cam block 116 is friction mounted within openings 92, 101 of the holders 90, 100 with its bottom surface co-planar with the bottom surface 91 of holder 90. Lug 123 extends down into cam lug slot 82 of knife 54 shown in FIG. 14.

Cam block 116 has T-shaped slot 124 mutually perpendicular to the axis of rotation of the shaft 114 and the plane of reciprocation of the knife 54 and is fixed relative to knife 54. The T-shaped cam 122 has cam slot 121 therein also perpendicular to shaft 114 and the plane of reciprocation of the knife. The T-cam 122 is slidably reciprocally mounted in the T-slot 124. The eccentric 120 is slidably and rotatably received within the cam slot 121 whereby rotation of the shaft 114 is translated to reciprocation of the knife edge 81.

Also shown in FIG. 26 is a console 130 with vacuum line 131 connected to vacuum control knob 132 and vacuum source 133, coil wires 134 connected to current control knob 135 and a power source 136, and motor wires 137 connected to motor control 138.

Also shown is a logic board 139 which can provide a variety of functions.

The console 130 provides several functions. From the console, the vacuum from vacuum pump 133 may be varied from 18 to 25 inches of mercury with the suction ring affixed to the cornea. Knob 132 controls a 24 volt vacuum pump 133 to maintain exact vacuum as selected. The console provides an automatic alarm and shutoff if the vacuum falls below a set amount. It provides for automatic release of vacuum after the drive motor moves a preset distance. The oscillation of the knife is varied by the speed of the drive motor 113 from 5000–30,000 rpm. An indication of the rpm is provided. The console will automatically deenergize the drive motor after it moves the knife the preset distance. The console will retract and reset drive motor to original position and provide an alarm or deactivation of the drive motors if not in reset position.

Operation of the device is simple. The physician places a custom made insert such as insert 48 into the cutting instrument 110. The physician then places the instrument 110 over the patient's eye with the insert 48, which is made of a clear material, over the cornea. The physician centers the insert on the exact center of the optical zone and activates the partial vacuum 132. The physician then activates the drive knob 138 which turns on the blade motor, and activates the coil control knob 135 which automatically advances the blade drive a preset distance. When the blade advances to the preset point, the motor 113 and advancer 111 are automatically turned off and the partial vacuum 131 is released. The entire procedure from centering of the optical zone to the completion of the cut should take no more than 20 seconds. A patch is placed over the patient's eye and the operation is complete.

Figure 28:
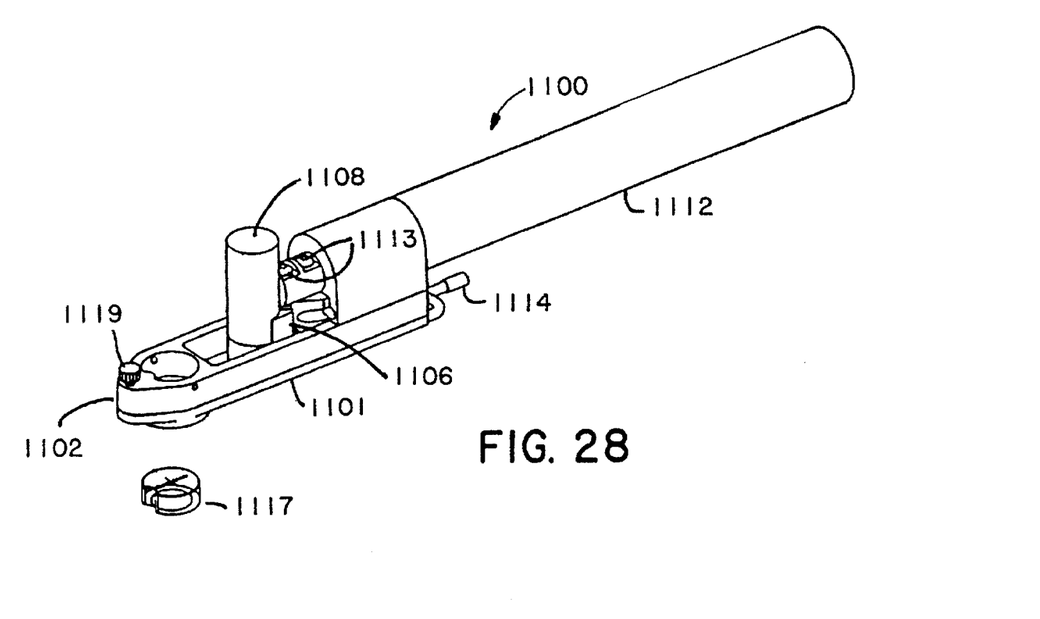
FIG. 28 is an isometric view of a second embodiment of the invention with an insert shown below.
Figure 29:
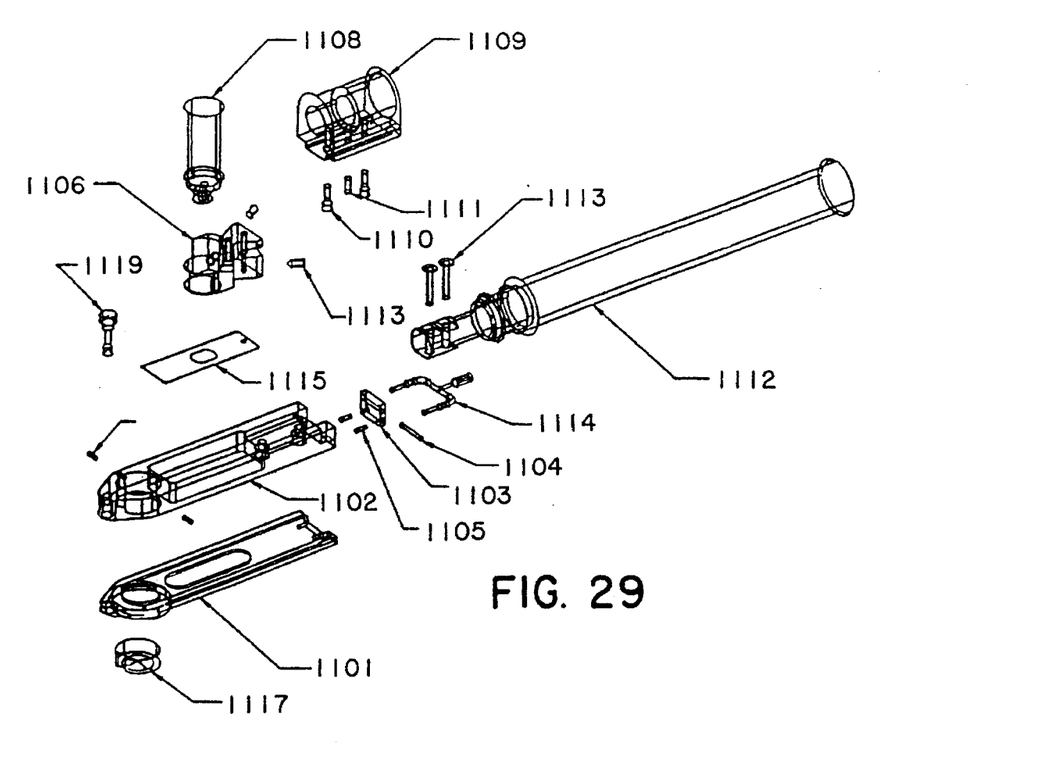
FIG. 29 is an exploded assembly drawing of the embodiment of FIG. 28 illustrating in schematic form each of the components forming the second embodiment.

Turning now to FIGS. 28 and 29, a second embodiment 1100 of the invention is shown. All the components to assemble the device 1100 are shown in the exploded assembly drawing of FIG. 29. As shown in FIGS. 28 and 29, device 1100 includes a single piece body 1102 which carries a pin registration plate 1103. The plate 1103 has two registration pins 1105 which are press fit into apertures in the plate 1103. Plate 1103 is retained on base 1102 by means of a locking pin 1104 which is pressed into corresponding apertures in plate 1103 and body 1102.

A suction plate 1101 is assembled to the body 1102 at one end by means of two apertures which engage the pins 1105. At the other end, the suction plate is retained on the body by means of a retaining screw 1119 which extends through the body 1102. Captured between the suction plate 1101 and the body 1102 is the optical insert 1117 and a knife 1115. The knife 1115 and the insert 1117 are for purposes of clarity not shown in 29 in the actual positional relationship relative to the body 1102 and the plate 1101. An actuator holder 1109 is fastened to the base 1102 by means of screw fasteners 1110. A linear actuator 1112 is captured in and supported in the holder 1109. A set screw 1111 is used to secure the actuator in position. The suction plate includes through bores which are in communication with apertures in the vicinity of the suction ring to form a suction chamber. The through bores exit the rear of the suction plate and are connected to a vacuum source by, for example, a vacuum manifold 1114.

The actuator 1112 has a piston 11121 extending from its one end. A motor holder 1106 is secured to the piston 11121 by means of fasteners 1113. The motor holder 1106 carries a blade drive motor 1108. The motor holder also carries the knife 1115 on its bottom surface.

The linear actuator 1112 serves to advance the knife 1115 such that knife 1115 traverses the area of the suction ring plate 1111 which carries the suction ring. While the knife 1115 is advanced, the blade motor 1108 drives the knife 11115 such that the leading edge of the knife oscillates from side to side.

Figure 30:
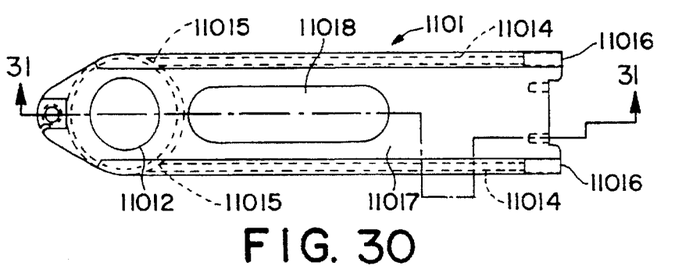
FIG. 30 is a top view of a suction plate.
Figure 31:
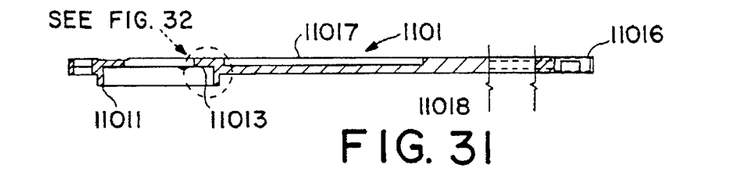
FIG. 31 is a side view of the plate of FIG. 30 taken in cross section along lines 31—31.
Figure 32:
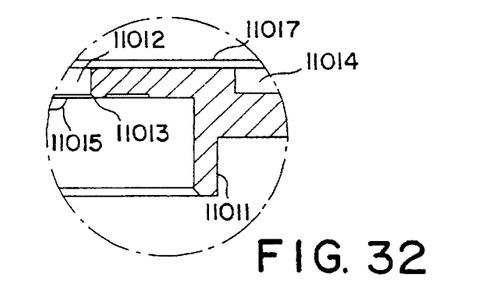
FIG. 32 is a detail of the circled portion of FIG. 31.

Turning now to FIGS. 30, 31 and 32, the suction ring plate 1101 is similar to that shown and described in the first embodiment description. The plate 1101 includes a suction ring 11011. Suction ring 11011 has a stepped portion produced by an inner aperture 11012 in the plate 1101. A square corner or shoulder 11013 is formed which will exert a force against the sclera of an eye. This force in conjunction with the forces exerted by the peripheral edge of suction ring 11011 against the eye will cause the eye to generate equilibrium forces which urge the eye into contact with the insert 1117. The aperture 11012 has a diameter which is smaller than the diameter of the prescriptive insert 1117 which is positioned above the aperture 11012. The plate 1101 includes two through bores 11014. Bores 11014 have one end which opens into the interior of the suction ring 1101 at openings 11015 and at the other end each has a port 11016 which receives the vacuum manifold 1114. As shown in FIG. 32, beveled edges are used at the edges of the suction ring 11011 and shoulder 11013. The suction plate includes a recess 11017 in its top surface. The recess 11017 is sized to receive the knife 1115 and to retain the knife in planar position such that it may be moved forward and back in reciprocating movement within the plane immediately above the suction ring 11011 and immediately below the insert 1117. The recess is of a width such that the knife 1115 may also pivot from side to side within the same plane as the reciprocating movement. A second recess 1108 is provided which allows the pivot pin 11061 which extends downward from the motor holder 1106 to freely slide back and forth as the knife 1115 is advanced and retracted.

Figure 33:
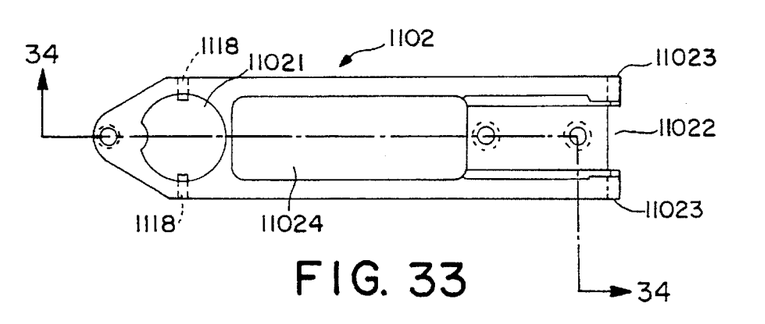
FIG. 33 is a top view of the body member.
Figure 34:
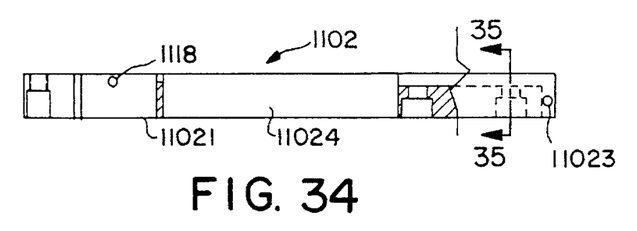
FIG. 34 is a side view of the body member of FIG. 33 taken in partial cross section along lines 34—34.
Figure 35:
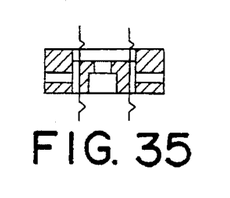
FIG. 35 is a cross section view of the body member taken along lines 35—35 in FIG. 34.

The one piece body assembly 1102 is shown in detail in FIGS. 33, 34 and 35. The body 1102 includes an insert receiving aperture 11021. The rear portion of the body 1102 includes a recess 11022 which receives the pin registration plate 1103. The recess is sized such that the plate 1103 is firmly held in place. A pin 1104 is inserted through apertures 11023 to retain the plate 1103. The plate 1103 has two registration pins 1105 which are received in corresponding apertures in the suction plate 1101. The other end of the suction plate 1101 is removeably retained against the bottom of the body 1102 by means of screw 1119 which is received in bore 11023. Body 1102 has a central aperture 11024 in which the motor holder 1106 and the blade drive motor 1108 may reciprocate back and forth. The body 1102 includes apertures 11024 which receive screws that fasten the actuator holder 1109 to the body 1102.

Prior to assembling the suction plate 1101 to the body 1102, the prescriptive insert 1117 is slid into the aperture 11021. Stop pins 1118 carried in the body 1102 limit the movement of the insert 1117 in the upward axial direction. When the suction plate 1101 is coupled to the base 1102, the suction plate 1101 prevents movement of the insert 1117 in the axial downward direction. Thus the insert 1117 is captured in the body 1102. It should be noted that although stop pins are utilized in this embodiment, the through bore aperture 11021 could be stepped to provide a shoulder against which the upper surface of the insert 1117 rests. In addition, the knife 1115 is captured between the body 1102 and the suction plate 1101.

Figure 36:
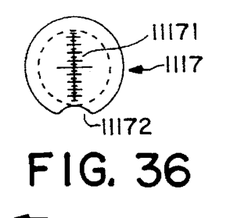
FIG. 36 is a top view of an insert used in the device of FIG. 27.
Figure 37:
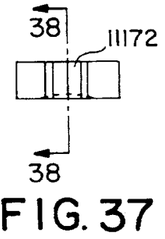
FIG. 37 is a side view of the insert of FIG. 36.
Figure 38:
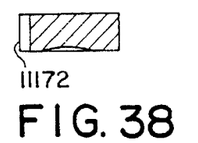
FIG. 38 is a cross section view of the insert taken along lines 38—38 in FIG. 37.

The insert is shown in FIGS. 36, 37 and 38. The insert 1117 of this embodiment includes an alignment scale 11171 which is laser etched into its upper surface, along with cross hairs. Rather than utilizing registrators as were employed in the first embodiment to provide registration of the insert, this embodiment utilizes a keyway 11172 integrally formed in the insert 1117 which engages a corresponding lug 11025 on the body 1102 to provide precise registrator of the insert 1117 in device 1100. Alternatively, the keyway or groove 11172 may extend axially only over a portion of the insert rather than along its entire length. In this alternate instance, the lug would be no longer than the keyway or groove and could be a pin rather than a lug.

Figures 39, 39A, 40, 41, 42, 45, 46, 47, 48, 49, 50:
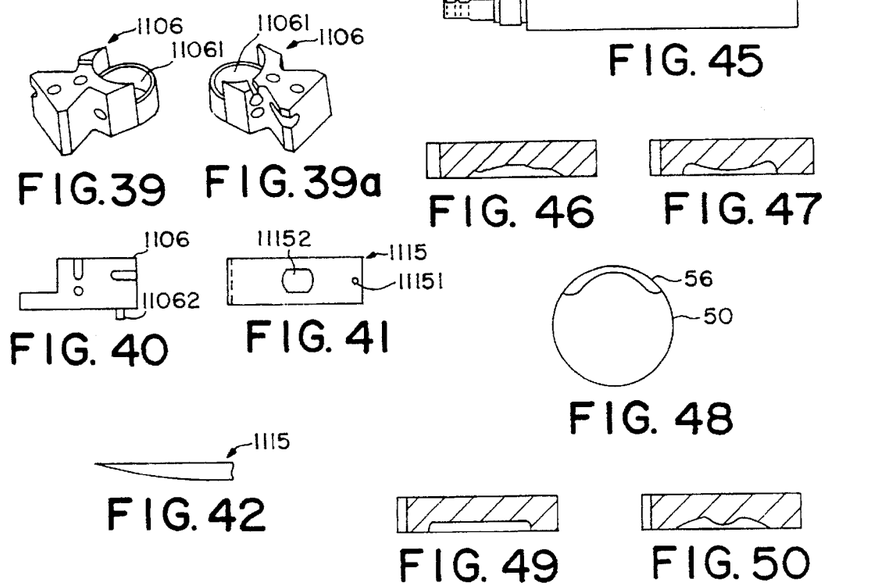
FIGS. 39 and 39a show the motor holder in right and left side isometric views.
FIG. 40 is a side view of the motor holder.
FIG. 41 is a top planar view of the knife utilized in the second embodiment.
FIG. 42 is an enlarged view of the edge of the knife of FIG. 41.
FIG. 45 shows the linear actuator.
FIG. 46 illustrates an insert having an irregular correction formed therein.
FIG. 47 illustrates an insert which produces a negative meniscus to correct for hyperopia.
FIG. 48 illustrates the resulting cut on the eye from using the insert of FIG. 47.
FIG. 49 illustrates an insert for producing a lamellar cut.
FIG. 50 illustrates an insert providing two prescriptive corrections.

The motor holder is shown in FIGS. 39 and 40. Motor holder 1106 includes a motor receiving ring 11061 to receive the blade motor 1108.

A linear actuator 1112 is secured to the device 1100 by utilizing the actuator holder 1109. The linear actuator is a commercially available device and includes a piston 11121 which extends from the actuator 1112 and which is coupled to the motor holder 1106 by fasteners 1113.

The motor 1108 carries a bearing 11082 on its shaft 11081 which engages a slot 11152 in the knife 1115. The bearing is pressed onto the shaft 11081 such that it is off center to form an eccentric. It should be noted that alternatively the shaft 11081 could have its end machined into an eccentric. With the rear end of the knife pinned to the holder 1106, the rotation of the eccentric in the groove 11152 in the knife 1115 will cause the front edge of the knife 1115 to swing from side to side in an arc.

Figure 43:
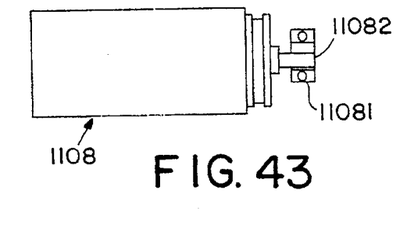
FIG. 43 is a side view of the knife motor.
Figure 44:
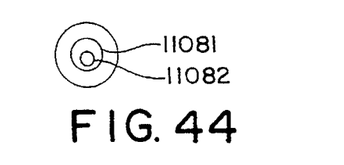
FIG. 44 is an end view of the eccentric of the motor of FIG. 43.

The knife motor 1108 is shown in FIG. 43. The shaft 11082 of the motor 1108 terminates eccentric 11081 which engages the aperture 11152 of the knife 1115.

The knife 1115 is shown in detail in FIGS. 41 and 42. The knife includes a pivot hole 11151 which engages a pivot pin of the motor holder 1106. The knife also includes an aperture 11152 which receives an eccentric 11081 on the output shaft 11082 of motor 1108. Aperture or slot 1152 is of a width corresponding to the diameter of the eccentric 11081 and a length which is at least twice the distance of the axis of the eccentric to its furthest point. By utilizing an eccentric in conjunction with a pivot, as the motor shaft 11082 turns, the knife 1115 will swing side to side through an arc to enhance cutting as the knife is reciprocally advanced.

Operation of this second embodiment is substantially the same as that of the first embodiment. As with the first embodiment, only the knife traverses the prescriptive insert 1117.

It has been found that the knife 1115 is ideally formed of zirconium. Zirconium is particularly advantageous because with zirconium, an extremely smooth and flat upper surface may be obtained on the knife 1115. With zirconium the top of the cutting edge may be made flat and the bottom surface 11151 may be beveled so that a chisel edge is found to achieve extremely smooth cuts. In contrast, with stainless steel, as the knife is sharpened a wire is formed along the cutting edge. This wire may be eliminated by back stropping of the edge. However, after backstropping, the top edge of the knife will be concave. With the top edge concave, cuts of the cornea will not have the prescriptive accuracy desired.

The control console for this second embodiment includes circuitry which will automatically stop the linear actuator to provide for automatic stopping of the knife 1115.

As pointed out there are numerous prescriptive corrections which may be made utilizing the device of the present invention. For example, FIG. 46 shows how one insert 1171 might be shaped in profile for an irregular correction. FIG. 47 illustrates a negative meniscus cut which will correct for hyperopia and the resulting cut 471 which is produced in an eye 50 is shown in FIG. 48. FIG. 49 illustrates an insert which will produce a lamellar cut. FIG. 50 illustrates how an insert which provides multifocal corrections may be shaped.

To fully appreciate the present invention, it is helpful to understand how the existing surgical techniques obtain optical correction of the refractive errors of the eye.

The first Keratomeliesus procedure involved removing tissue from the cornea, freezing it, placing it on a lathe and reshaping it, and returning the tissue to the corneal surface. This procedure evolved into an in-situ procedure known as KMIS (Keratomelieusus In-Situ) in which two concentric lamellar disks are removed from the corneal surface. By returning the first tissue to the surface of the eye in the absence of the second, optical correction is achieved.

In Radial Keratotomy (RK), radial incisions are made on the anterior cornea, weakening the structure enough that the internal pressures of the eye will flatten out the central cornea, reducing nearsightedness. With the advent of the excimer laser, a new technique known as Photo Refractive Keratectomy (PRK) which reshapes the anterior of the cornea through tissue ablation was introduced.

Although other corrective techniques exist, the three surgical procedures identified are the most commonly used.

Figure 51A:
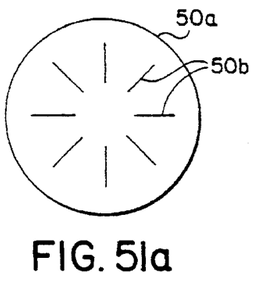
FIGS. 51a and 51b illustrate the prior art radial keratometric correction of myopia.
Figure 51B:
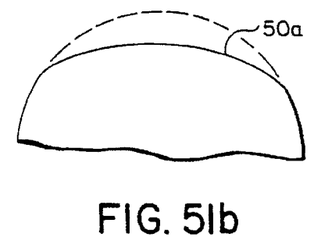

Radial Keratotomy ia a technique which introduces radial incisions into the anterior surface of the cornea. These incisions penetrate to a depth of 90% of the cornea thickness, weakening the structure and allowing the intraocular pressure of the eye to flatten the cornea. FIGS. 51a and 51b illustrate the RK procedure. FIG. 51a illustrates the cornea 50a of an eye with the radial cuts 50b. FIG. 51b illustrates the eye 50 in schematic cross-section to show the original curvature of the eye in dashed line and the flattening of the eye as a result of the RK surgical cuts. Flattening of the central cornea reduce its optical power, thereby correcting for nearsightedness (myopia). Hexagonal incisions may also be made, allowing for correction of astigmatism.

The amount of optical correction achieved is a function of the number and depth of cuts as well as the length of cuts and the optical zone from which they originate. There are no optical equations for radial keratotomy which may be used to calculate the number or length of cuts which will correct for a given refractive error. Instead, refractive surgeons utilize a nomogram in order to determine the parameters relative to the cuts. The nomogram specifies the number of incisions and the optical zone from which they should originate in order to correct for a known refractive error as specified in diopters (D). These nomograms are empirically derived, and hence rely upon postoperative statistics to determine future parameters.

In PRK, an excimer laser of 193 nm wavelength is used to ablate corneal stromal tissue, reshaping the anterior surface of the cornea. Unlike radial keratotomy, the excimer laser corrects for refractive error in an optically correct fashion. Through controlled ablation of the corneal tissue, the anterior radius of the cornea may be modified to obtain a specific correction in diopters. However, to ablate the stromal tissue, the outermost layer of the cornea, the epithelium must be first mechanically removed. This induces moderate to severe postoperative pain which persists until the epithelium can regenerate over the open wound.

Figure 52:
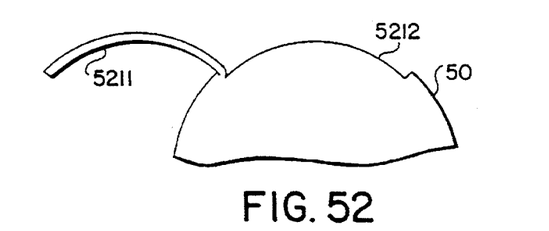
FIG. 52 illustrates the prior art LASIK correction for myopia.

In a procedure known as LASIK (Laser In-Situ Keratomelius) illustrated in FIG. 52, a lamellar disk 5211 containing the epithelium is first excised from the corneal surface of eye 50. This lamellar disk is not completely removed, but flapped to ensure that the tissue is not lost during the procedure. The laser is used to ablate tissue 5212 from the eye 50. The corneal ablation is performed on the underlying stroma as in PRK and the anterior radius of the cornea is thereby modified to provide correction.

Figure 53A:
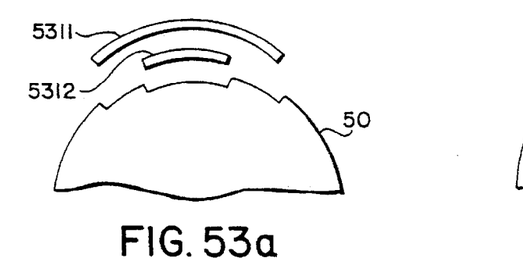
FIGS. 53a and 53b illustrate the prior art Lamellar Keratoplastic correction for myopia.
Figure 53B:
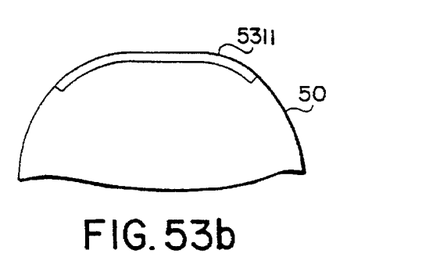

Lamellar Keratectomy as illustrated in FIGS. 53a and 53b requires removing two concentric, lamellar disks 5311 and 5312 from the anterior corneal surface of eye 50, the second disk 5312 being smaller in diameter than the first disk 5311. The devices which remove these lamellar tissues are known as microkeratomes. Optical correction is achieved by replacing the first disk 5311 onto the eye surface in the absence of the second disk 5312 as shown in FIG. 53b. The first disk 5311 will fall into the abscess created by the second and a flattening of the cornea results. The amount of optical correction which is achieved is controlled by both the diameter and thickness of the second disk 5312. As in radial keratotomy, there are no optical equations which may be used to determine these parameters. An empirically derived nomogram must be used to specify what diameter and thickness the disks must be in order to obtain a specific refractive error correction.

Each of the above described procedures suffers in that each is limited by the range of refractive error that can be corrected. A recent poll of surgeons at the International Society of Refractive Surgery indicated that radial keratotomy is used to correct for myopic refractive errors from 0 to 3 diopters, PRK from 4 to 6 diopters, and Lamellar Keratoplasty is used for any refractive errors above 6 diopters.

Figure 54:
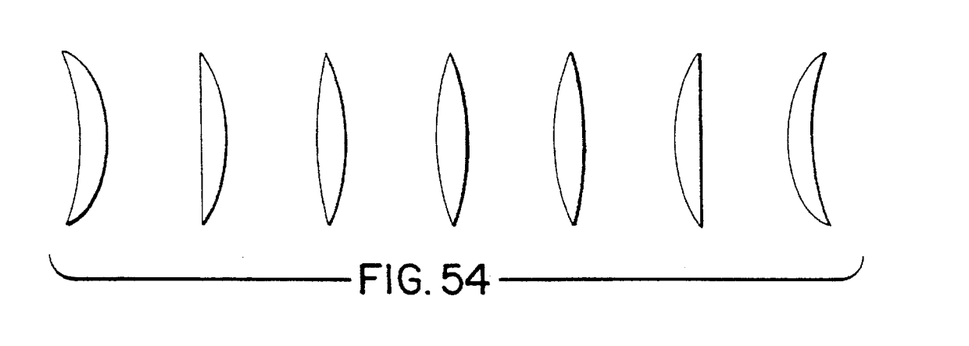
FIG. 54 illustrates different shaped lenses all of the same optical power.

The keratome of the present invention provides an optically correct mechanical technique for obtaining emmetropia. The technique is based on the theory of optical lens bending as shown in FIG. 54 which illustrates lenses with spherical surfaces all of the same paraxial focal length, i.e., all of the lenses shown have equivalent optical power yet have different shape factors "q", known as the Coddington shape factor. This shape factor is defined by $$q=(r2+r1)/(r2-r1)$$

where r1 and r2 are the radii of curvature of the first and second surfaces of the lens. FIGS. 1 through 6 as previously described illustrate how light bending theory is used to provide for the removal of a positive meniscus lens for the correction of myopia.

Turning now to FIG. 55, a significant new procedure for corrective eye surgery is shown. FIG. 55a illustrates the prescriptive correction to be made to a cornea. The prescriptive correction is in the form of a positive meniscus. The positive meniscus is mathematically converted to a planoconvex lens shape in FIG. 55b. The negative image of this shape is ground into an optical insert shown in FIG. 55c. The insert is to be used in the keratome of my invention. In addition, a second insert is prepared which is in the shape of a lamellar disk of a thickness of slightly greater than that of the epithelium. This second insert is shown in FIG. 55d.

Figure 55A:
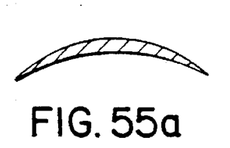
FIGS. 55a through 55h illustrate one refractive corrective procedure in accordance with the principles of the invention.
Figure 55B:
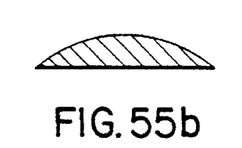
Figure 55C:
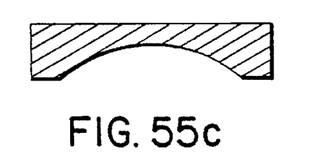
Figure 55D:
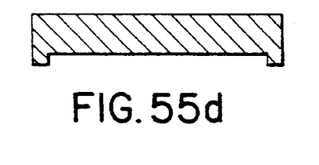
Figure 55E:
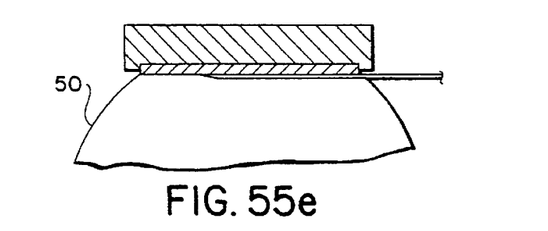
Figure 55F:
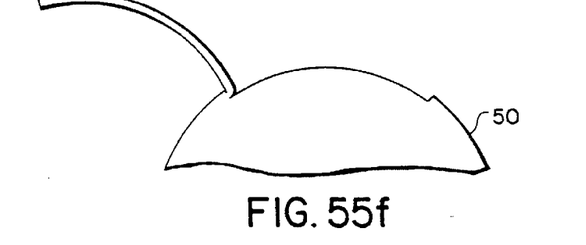
Figure 55G:
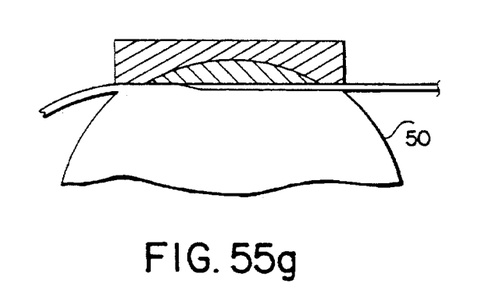
Figure 55H:
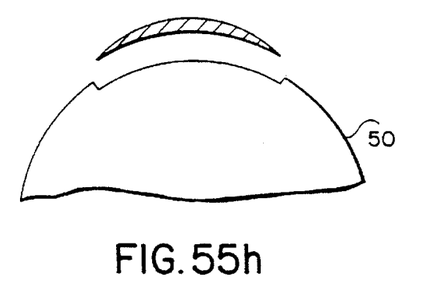

In operation, the surgeon first places the universal keratome of the invention on the patient's eye. The keratome will have the lamellar disk insert. The keratome is positioned over the eye such that the lamellar disk insert is centered over the eye. The surgeon will then operate the keratome to apply vacuum to the eye. The eye will then be urged into contact against the insert as shown in FIG. 55e. The surgeon will then operate the keratome to advance the cutting knife across the insert as shown in FIG. 55e, having selected the cut to be such that a flap will be cut. The knife will be retracted. The vacuum is then released, and the keratome is removed from the eye. The resulting lamellar disk flap will be moved to the side as shown in FIG. 55f. The surgeon will then place a keratome carrying the insert having the prescriptive correction on the patient's eye, with the insert centered on the eye. The surgeon will again cause vacuum to be applied to the suction ring of the keratome causing the eye to again be urged into contact with the corrective insert as shown in FIG. 55g. The surgeon will operate the keratome to advance the knife and excise the corrective disk. The surgeon will then remove the vacuum. The keratome will then be removed from the patient's eye. The eye will then have the corrective cut shown in FIG. 55h and, as shown, the flap is replaced over the cornea.

The keratome and the procedure has been tested on six fresh, human cadaver eyes. The testing consisted of first performing a 9 mm diameter, 160 micron thick lamellar flap followed by a second concentric myopic or hyperopic resection. The myopic and hyperopic resections consisted of four 10 diopter myopic tissue resections at 5.5 mm diameter; one 30 diopter myopic tissue resection at 5.5 mm diameter; and one −30 diopter hyperopic tissue resection at 5.5 mm diameter.

The excised tissues were prepared for scanning electron microscopy following a 36 hour fixation period. Similarly, the corneal caps from which the tissues had been excised were removed from the donor globes and prepared for scanning electron microscopy. The excised tissues, which represent the optical correction achieved, were cut through the median and examined in cross section to verify their meniscus shapes. The corneal caps were examined laterally to demonstrate the smoothness of the cut. The results of the examination was verification of the removal of the positive and negative meniscus lenses for the correction of myopia and hyperopia, respectively.

In refractive surgery, it is desirable to remove as little tissue as possible and still obtain the required amount of optical correction. By reducing the amount of tissue removed, the stability of the cornea following the procedure will be improved. Since the cornea is 560 microns thick, no more than 300 microns should be removed in the corrective cuts to maintain stability. In the procedure and apparatus of the invention, for optical zones of up to 30 diopters of error for both myopia and hyperopia can be corrected without violating the thickness restriction.

In yet a further method in accordance with the invention, the keratome may be utilized to produce a lamellar flap for removal and replacement of the epithelium prior to use of LASIK or Lamellar Keratectomy. In addition, the lamellar disk may be completely excised rather than left as a flap, and then replaced after laser ablation.

The foregoing description of preferred embodiments have been presented for the purposes of illustration and description. It is not intended to limit the invention to the embodiments disclosed. As will be apparent to those skilled in the art, many modifications and variations are possible in the light of the above teaching without departing from the spirit or scope of the invention. It is intended that the scope of the invention be limited only by the claims appended hereto.

What is claimed:

1. A method of performing corrective eye surgery comprising the steps of:

determining a desired prescriptive correction for a patient's eye;

cutting a first disk to remove the epithelium of said eye, said first disk being formed as a flap;

excising a second disk from said eye, said second disk being shaped to provide said desired prescriptive correction; and replacing said first disk on said eye.

2. A method in accordance with claim 1 wherein:

said first disk is of a first diameter;

said second disk is of a second diameter, said second diameter is less than said first diameter.

3. A method in accordance with claim 2 wherein:

said prescriptive correction includes myopia.

4. A method in accordance with claim 2 wherein:

said prescriptive correction includes hyperopia.

5. A method in accordance with claim 1, wherein:

said first disk is a lamellar shape.

6. A method in accordance with claim 5, wherein:

said second disk is one of a positive or negative meniscus shape.

7. A method of performing refractive surgery comprising the steps of:

determining a prescriptive correction for a patient's eye:

utilizing said prescriptive correction to determine an equivalent planar corrective shape;

placing a surgical device on said eye, said surgical device having a first element which has a first surface portion shaped to define a lamellar disk of a thickness greater than the epithelium of said eye;

causing said eye to be urged into contact with said first surface portion;

causing a knife edge to traverse said first element adjacent said first surface portion to excise a disk shaped portion of said epithelium of said eye;

removing said surgical device from said eye;

replacing a surgical device on said eye, said surgical device having a second element which has a second surface portion corresponding to a said planar corrective shape;

causing said eye to be urged into contact with said surface portion;

causing a knife edge to traverse said second element adjacent said second surface portion to excise the portion of said eye in said second surface portion; and removing said surgical device from said eye.

8. A method in accordance with claim 7, including the steps of:

operating said surgical device such that said knife edge leaves said lamellar disk shaped portion attached to said eye to form a flap;

moving said flap off the surface from which it had been excised prior to replacing a surgical device on said eye; and replacing said flap over said eye after excising the portion of said eye in said second surface portion.

9. A method of performing refractive surgery comprising the steps of:

determining a prescriptive correction for a patient's eye:

placing a surgical device on said eye, said surgical device having a first element which has a first surface portion shaped to define a disk of a thickness greater than the epithelium of said eye;

causing said eye to be urged into contact with said first surface portion;

causing a knife edge to traverse said first element adjacent said first surface portion to excise a disk shaped portion of said epithelium of said eye;

limiting the distance traversed by said knife edge such that a flap is formed which is attached to the eye;

removing said surgical device from said eye;

replacing a surgical device on said eye, said surgical device having a second element which has a second surface portion corresponding to a said planar corrective shape;

causing said eye to be urged into contact with said surface portion;

causing a knife edge to traverse said second element adjacent said second surface portion to excise the portion of said eye in said second surface portion;

removing said surgical device from said eye; and placing said flap over said eye.

10. A method in accordance with claim 9, wherein:

said prescriptive correction includes myopia.

11. A method in accordance with claim 9, wherein:

said prescriptive correction includes hyperopia.

12. A method in accordance with claim 9, wherein:

said excised portion has a thickness less than 300 microns.

13. A method of performing refractive surgery comprising the steps of:

placing a keratome device on an eye, said keratome device having an element with a surface portion recess the depth of at least the epithelium of said eye;

operating said keratome device such that vacuum is applied to said eye urging said eye into contact with said recess;

operating said keratome device in an automatic mode such that a knife edge traverses said element to excise a flap, said knife edge being stopped before said flap is severed;

removing said keratome device;

utilizing a laser to remove corneal tissue to produce a prescriptive correction; and replacing said flap.

* * * * *

Disclaimer 5,658,303—Russell G. Koepnick, 4435 N. 78th St. #113A, Scottsdalp, Ariz. 85251. UNIVERSAL AUTOMATED KERATECTOMY APPARATUS AND METHOD. Patent dated August 19, 1997. Disclaimer filed on January 7, 2003, by the Inventor.

Hereby enters this disclaimer to claim 13, of said patent.

*(Official Gazette, July 22, 2003)*